US00PP19836P2

(12) United States Plant Patent
Hofmann

(10) Patent No.: US PP19,836 P2
(45) Date of Patent: Mar. 17, 2009

(54) **NEW GUINEA *IMPATIENS* PLANT NAMED 'FISUPNIC KIRMAG'**

(50) Latin Name: *Impatiens hawkeri*
Varietal Denomination: Fisupnic Kirmag

(75) Inventor: Birgit Christa Hofmann, Bendorf (DE)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 12/077,915

(22) Filed: Mar. 21, 2008

(51) Int. Cl.
*A01H 5/00* (2006.01)

(52) U.S. Cl. ..... Plt./318.6
(58) Field of Classification Search ..... Plt./318.6
See application file for complete search history.

*Primary Examiner*—Annette H Para
(74) *Attorney, Agent, or Firm*—S. Matthew Edwards

(57) ABSTRACT

A new New Guinea *Impatiens* plant particularly distinguished by large, nearly round, brilliant, purple-red-colored flowers, medium green foliage, relatively narrow leaves, a mounded, semi-spherically shaped, moderately tight plant habit and medium flowering response, is described.

1 Drawing Sheet

Genus and species: *Impatiens hawkeri* W. Bull.
Variety denomination: 'Fisupnic Kirmag'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisupnic Kirmag'. The new cultivar originated from a hybridization made in the year 2003 in Hillscheid, Germany. The female parent was the proprietary New Guinea *Impatiens* plant 'K03-3186-1' (unpatented), while the male parent was the proprietary *Impatiens* plant 'K03-2428-2' (unpatented). The seeds produced by the hybridization were sown in a greenhouse in Moncarapacho, Portugal in the fall of 2003. A single plant selection was chosen for further evaluation and for asexual propagation in the spring of 2004 in Portugal.

The new cultivar was created in 2003 in Hillscheid, Germany and has been asexually reproduced repeatedly by vegetative cuttings and tissue culture in Moncarapacho, Portugal and Hillscheid, Germany over a three-year period. 'Fisupnic Kirmag' has not been observed under all possible environmental conditions. The phenotype may vary significantly with variations in environment such as temperature, light intensity and day length, without, however, any variation in genotype. The present invention has been found to retain its distinctive characteristics through successive asexual propagations.

Plant Breeder's Rights for this cultivar were applied for in Canada on Mar. 30, 2007, and in Switzerland, on May 23, 2007. 'Fisupnic Kirmag' has not been made publicly available more than one year prior to filing of this application.

SUMMARY OF THE INVENTION

The following are the most outstanding and distinguishing characteristics of this new cultivar when grown under normal horticultural practices in Hillscheid, Germany, and in Langley, British Columbia, Canada.

1. Brilliant, purple-red flower color;
2. Large flowers, nearly round;

3. Medium green foliage with relatively narrow leaves;
4. Mounded, semi-spherically shaped, moderately tight plant habit; and
5. Medium flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13 to 14 weeks old, grown in a greenhouse in Hillscheid, Germany, in the spring of 2007.

DESCRIPTION OF THE NEW CULTIVAR

The following detailed description sets forth the distinctive characteristics of 'Fisupnic Kirmag'. The data which defines these characteristics were collected from asexual reproductions carried out in Hillscheid, Germany. The plant history was taken on 10- to 12-week-old plants which were planted as rooted cuttings in 12-cm pots in late February 2007, and then grown in a greenhouse at a minimum temperature of 16° C. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K03-3186-1' a proprietary, cherry-red-flowered New Guinea *Impatiens* plant (unpatented).
*Male parent.*—'K03-2428-2' a purple-flowered proprietary New Guinea *Impatiens* plant (unpatented).

Growth:

*Growth and branching habit.*—Tall, mounded, moderately tight; the growth is indeterminate, though weak after the beginning of flowering.

*Height.*—17.2 cm.

*Width.*—31.8 cm.

*Propagation.*—Terminal tips for cuttings.

*Time to produce a finished flowering plant.*—9 to 10 weeks for a 12-cm pot.

*Time to initiate and develop roots.*—About 18 days at 22° C.

Branches:

*Average number.*—7.

*Length of branches.*—About 12 cm to 15 cm.

*Internode length.*—About 3.0 cm to 5.5 cm.

*Diameter of branches.*—0.7 cm to 1.2 cm.

*Stem color.*—RHS 185A middle part to RHS 187C (purple) shoot tips.

Leaves:

*Arrangement.*—Primarily in whorls.

*Size.*—Length: 14.4 cm. Width: 5.4 cm.

*Shape.*—Lanceolate to elliptic.

*Margin.*—Slightly serrate, ciliated.

*Apex.*—Acuminate.

*Base.*—Acute.

*Color (mature leaves).*—Upper surface: RHS 137A to RHS 137B. Lower surface: Between RHS 138A and RHS 138B.

*Color (immature leaves).*—Upper surface: RHS 137C. Lower surface: RHS 138B.

*Texture.*—Upper surface: Glabrous, smooth to rugose, dull to slightly glossy. Lower surface: Glabrous with protruding veins.

*Venation color.*—Upper surface: RHS 47B near base, fading towards leaf tip. Lower surface: RHS 187C (purple).

*Variegation.*—None.

*Petioles.*—Length: 2.9 cm. Diameter 0.3 cm to 0.4 cm. Color: Upper surface: RHS 47A or RHS 53B (reddish). Lower surface: RHS 185A (purple). Texture: Glabrous.

Flower buds:

*Shape.*—Ovoid.

*Size.*—Length: 2.1 cm to 2.3 cm. Diameter: 1.3 cm to 1.5 cm.

*Color.*—RHS 53C (cherry-red).

Inflorescence:

*Blooming habit.*—9 to 10 weeks after planting of rooted cuttings.

*Inflorescence type.*—Flowers appear solitary in the leaf axiles of the upper nodes of the stems.

*Number of flowers per node.*—5 to 7, in various stages of development.

*Flowering season.*—Continuous but mainly from March to October, depending on light intensity.

*Lastingness of individual blooms.*—Up to 12 days (greenhouse, 18° C.).

*Peduncle.*—Color: RHS185A (brownish-purple). Size: Length: 6.5 cm. Diameter: 0.2 cm. Texture: Glabrous, flexible.

Flowers:

*Form of corolla.*—Single with 5 petals.

*Shape of corolla.*—Nearly round, with the petals overlapping, nearly flat.

*Corolla size.*—Initially very large, later diminishing a little. Length: 8.4 cm. Width: 8.3 cm. Depth: 1.2 cm.

*Fragrance.*—None.

Petals:

*Shape.*—Cordate, weakly lobed at the top.

*Apex.*—Weakly emarginate.

*Base.*—Attenuate.

*Margin.*—Entire.

*Petal size.*—Upper petal: Length: 3.4 cm. Width: 5.4 cm. Lateral petal: Length: 3.3 cm to 3.4 cm. Width: 4.3 cm to 4.5 cm. Lower petal: Length: 3.3 cm to 3.5 cm. Width: 4.8 cm to 4.9 cm.

*Color.*—General color description: Uniformly intense red-purple. Immature: Upper surface: Deeper than RHS N66A. Lower surface: RHS 61C. Mature: Upper surface: RHS N66A to RHS N66B. Lower surface: RHS 63A.

*Petal texture.*—Upper surface: Silky. Lower surface: Smooth, glabrous.

*Aspect.*—Mostly horizontally, mostly flat.

Calyx:

*3 to 5 sepals.*—One transformed into the spur, two lateral sepals, and the fourth and fifth fused (keel-like) with the underside of the banner petal.

*Spur shape.*—Downwardly curved.

*Color.*—RHS 53B (Red).

*Size.*—Length: 5.7 cm. Diameter: 0.3 cm at the flower base; 0.05 cm at the tip.

*Lateral sepals.*—Shape: Elliptic. Length: 1.5 cm. Width: 0.6 cm. Margin: Entire. Apex: Acuminate to caudate. Base: Rounded. Color: RHS 176D (brown), semi-transparent.

Reproductive organs:

*Stamens.*—Number: 5, fused, about 0.6 cm to 0.8 cm in diameter. Stamen color (upper surface): RHS 52A (rose-red). Anthers: Fused, hooded. Pollen color: RHS 8D (whitish-yellow).

*Pistils.*—Style and stigma: 5, very short, RHS 150D (pale yellow). Pistil length: 0.5 cm to 0.6 cm. Ovary color: RHS 143A (green).

Fruit and seed set: No seed set observed.

Disease and insect resistance: No particular resistance or susceptibility has been observed.

COMPARISON WITH PARENTAL AND COMMERCIAL CULTIVARS

'Fisupnic Kirmag' differs from the female parent 'K03-3186-1' (unpatented) by having a slightly more bluish-red flower color, rounder and larger flowers, and being more freely branching than 'K03-3186-1'.

'Fisupnic Kirmag' differs from the male parent 'K03-2428-2' (unpatented), by having a purple-red flower color while 'K03-2428-2' has a purple flower color. In addition, 'Fisupnic Kirmag' has a taller plant habit than 'K03-2428-2'.

'Fisupnic Kirmag' differs from the commercial cultivar 'Balcelichey' (U.S. Plant Pat. No. 15,805) by having a more bluish hue of flower color and rounder flowers, while 'Balcelichey' has weakly zygomorphic flowers. Additionally, plants of 'Fisupnic Kirmag' are taller, especially with regard to the height of the foliage.

'Fisupnic Kirmag' differs from the cultivar 'Fisimp 551' (U.S. Plant Pat. No. 13,702) by having somewhat larger and flatter flowers of a more intense color and medium green with light green underside foliage whereas 'Fisimp 551' has dark green foliage with purple undersides. Furthermore, the stems of 'Fisupnic Kirmag' have strong anthocyanin coloration (brown-purple), while those of 'Fisimp 551' are mainly green with only a weak infusion of anthocyanin.

I claim:

1. A new and distinct cultivar of New Guinea *Impatiens* plant as shown and described herein.

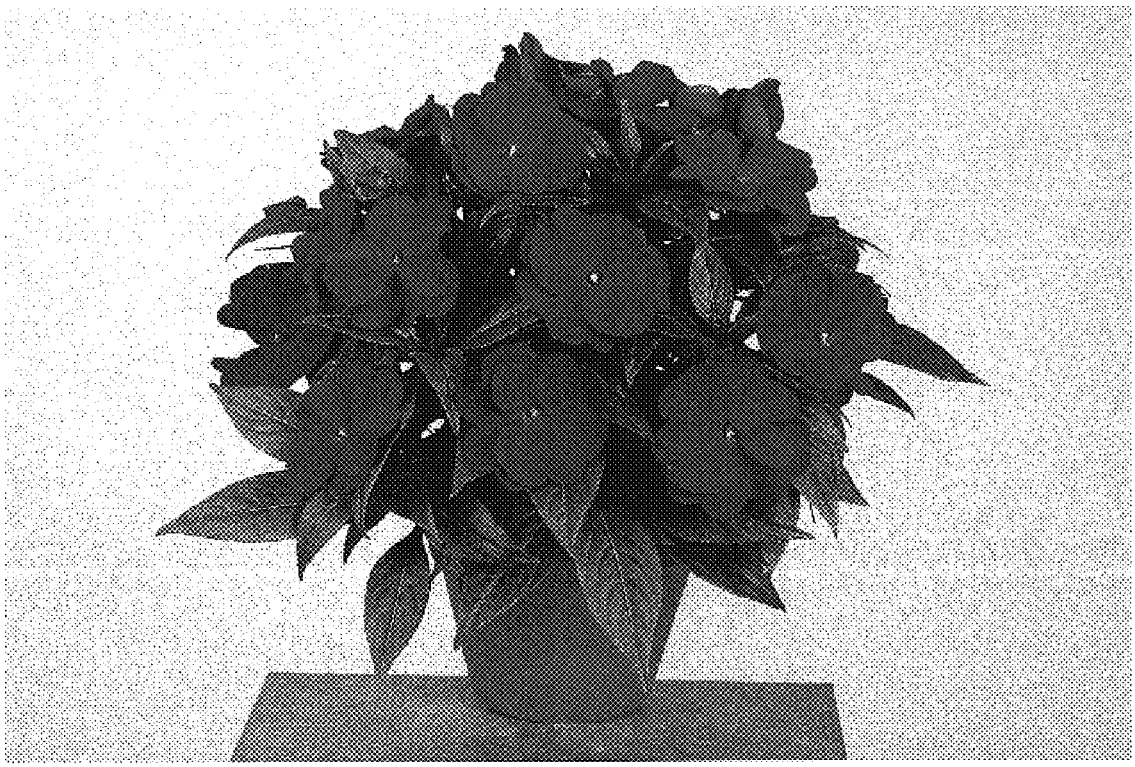

* * * * *